United States Patent [19]

Matsuoka et al.

[11] Patent Number: 5,407,826

[45] Date of Patent: Apr. 18, 1995

[54] ISOLATED CULTURES OF MICROORGANISMS OF CLONOSTACHYS CYLINDROSPORA, GLIOCLADIUM AND NECTRIA GLIOCLADIOIDES

[75] Inventors: Tatsuji Matsuoka; Nobufusa Serizawa, both of Tokyo; Tsuyoshi Hosoya; Kouhei Furuya, both of Tsukuba, all of Japan

[73] Assignee: Sankyo Company, Limited, Tokyo, Japan

[21] Appl. No.: 216,652

[22] Filed: Mar. 22, 1994

Related U.S. Application Data

[62] Division of Ser. No. 990,689, Dec. 15, 1992, Pat. No. 5,334,517.

[30] Foreign Application Priority Data

Dec. 17, 1991 [JP] Japan .................. 3-333353

[51] Int. Cl.$^6$ .................. C12N 1/14; C12P 13/24
[52] U.S. Cl. .................. 435/254.1; 435/107; 435/911
[58] Field of Search .................. 435/254.1, 911, 107

[56] References Cited

U.S. PATENT DOCUMENTS

| | | | |
|---|---|---|---|
| 3,892,629 | 7/1975 | Smith et al. | 435/242 |
| 4,642,131 | 2/1987 | Hoitink | 435/850 |
| 4,900,348 | 2/1990 | Hoitink | 435/252.1 |
| 5,120,652 | 6/1992 | Groeger et al. | 435/228 |
| 5,219,741 | 6/1993 | Groeger et al. | 435/107 |
| 5,223,415 | 6/1993 | Conder et al. | 435/125 |
| 5,256,547 | 10/1993 | Rudat et al. | 435/71.1 |

FOREIGN PATENT DOCUMENTS

| | | |
|---|---|---|
| 0072710 | 2/1986 | European Pat. Off. |
| 555475 | 8/1993 | European Pat. Off. |

OTHER PUBLICATIONS

Patent Abstract of Japan, vol. 16, No. 76 (C–0914), Feb. 25, 1992, of JP 03 226 995 (Kyowa Hakko Kogyo Co., Ltd.), Nov. 27, 1991.

Transactions of the Microbial Society of Japan, vol. 4, No. 4, 1963, pp. 83–90, K. Tsubaki, "Notes on the Japanese Hyphomycetes. I. Chloridium, Clonostachys, Ishmospora, Pseudobotrytis, Stachybotrys and Stephanoma", pp. 83–39.

Mycologia, vol. 49, 1957, pp. 529–533, E. B. Smalley, "The Perfect Stage of Gliocladium Roseum".

Tomoyuki Shibata et al, Heterocycles, *An International Journal for Reviews and Communications in Heterocyclic Chemistry*, "Synthesis of Optically Active 3–Mercaptopyrrolidine Derivatives, Synthetic Intermediates of Carbapenem RS–533 and Its Isomer" (1986), 24, No. 5.

Ramadasan Kuttan et al, "The Biosynthesis of Cis–4–Hydroxy–L–proline in Sandal", *Biochem. J.*, 117, 1013 (1970), pp. 1015–1017.

*Primary Examiner*—Herbert J. Lilling
*Attorney, Agent, or Firm*—Frishauf, Holtz, Goodman & Woodward

[57] ABSTRACT

Trans-4-hydroxy-L-proline is produced microbially, especially by the cultivation of a microorganism of the genus Clonostachys, Gliocladium or Nectria.

2 Claims, No Drawings

ISOLATED CULTURES OF MICROORGANISMS OF CLONOSTACHYS CYLINDROSPORA, GLIOCLADIUM AND NECTRIA GLIOCLADIOIDES

This is a division of application Ser. No. 07/990,689 filed Dec. 15, 1992, now U.S. Pat. No. 5,334,517.

BACKGROUND OF THE INVENTION

The present invention relates to a process for the production of trans-4-hydroxy-L-proline microbially, especially by the cultivation of a microorganism of the genus Clonostachys, Gliocladium or Nectria.

The systematic name of trans-4-hydroxy-L-proline is (2S, 4R)-(−)-4-hydroxypyrrolidine-2-carboxylic acid, but this compound is, as is common in the art, herein referred to by its trivial name "trans-4-hydroxy-L-proline". It is a known compound which is used commercially for the synthesis of a number of compounds, notably carbapenem antibiotics, and it may be represented by the formula (I):

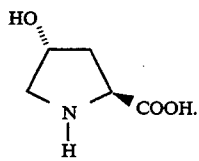

For example, starting from trans-4-hydroxy-L-proline it is possible to synthesize N-p-nitrobenzyloxycarbonyl-3-mercaptopyrrolidine or other synthetic intermediates [Heterocycles, 24, No. 5 (1986)], and this, in turn, can be used to prepare useful carbapenem antibiotics such as (5R,6S,8R)-6-(1-hydroxyethyl)-2-(pyrrolidin-3-ylthio)-2-carbapenem-3-carboxylic acid (Japanese Patent Publication No. Sho 61-29357).

trans-4-Hydroxy-L-proline is one of the protein constituents of collagen and of elastin, both of which are proteins present in the, connective tissue of animals. It is also present in the epidermal tissue of the earthworm in an amount which may be as much as 10 times the content of proline. Since it exists in such a large amount in collagen, it is commonly prepared from a gelatin hydrolysate by extraction and purification procedures. It has also been reported in certain higher plants, such as in the leaves of the sandalwood trees of the genus Santalum [Biochem. J. 117, 1013 (1970)]. However, the presence of free trans-4-hydroxy-L-proline has not previously been confirmed in microorganisms.

We have now found that microorganisms of the genera Clonostachys, Gliocladium and Nectria can produce trans-4-hydroxy-L-proline, which can be recovered from the culture medium in useful quantities.

BRIEF SUMMARY OF INVENTION

It is an object of the present invention to provide a process for the production of trans-4-hydroxy-L-proline by the cultivation of a microorganism.

It is a further object to provide such a process employing a trans-4-hydroxy-L-proline producing strain of the genus Clonostachys, of the genus Gliocladium or of the genus Nectria.

Thus, the present invention consists in a process for the preparation of trans-4-hydroxy-L-proline by cultivating a trans-4-hydroxy-L-proline producing microorganism, preferably of the genus Clonostachys, of the genus Gliocladium or of the genus Nectria, and separating the resulting trans-4-hydroxy-L-proline from the culture broth.

DETAILED DESCRIPTION OF INVENTION

The technology involved in the production of valuable materials using microorganisms has been known for a considerable time, and is well established. It is, therefore, of considerable commercial value to find a microbial source of trans-4-hydroxy-L-proline, which has not previously been achieved.

The microorganisms which we have so far found to produce useful quantities of the desired trans-4-hydroxy-L-proline are members of the genera Clonostachys, Gliocladium and Nectria, and particularly the strains which we identify as Clonostachys cylindrospora SANK 14591, Clonostachys sp. SANK 18192, Gliocladium sp. SANK 18092 and Nectria gliocladioides Smalley et Hansen SANK 17992.

We particularly prefer to employ as the microorganism used for the production of the desired trans-4-hydroxy-L-proline a strain of the species Clonostachys cylindrospora, and preferably the newly isolated strain identified as Clonostachys cylindrospora SANK 14591. This strain was isolated from fallen leaves collected in the City of Tsukuba, Ibaraki Prefecture, Japan, in April 1991.

Clonostachys cylindrospora SANK 14591 has been deposited under the terms of the Budapest Treaty at the Fermentation Research Institute, Agency of Industrial Science and Technology, Japan, on 25 Nov., 1991, under the accession Number FERM BP-3661.

Details of the microbiological properties of this strain are as follows.

Colonies on modified Weitzman and Silva-Hunter agar medium, whose composition is given below, achieved a diameter of 29 mm after growth for 7 days at 25° C. The surface of the colony was flat and powdery, in part because of sparse formation of aerial hyphae. The whole surface presented a nearly white coloration. Excellent formation of conidia was observed on almost the whole of the surface. After additional cultivation for 1 week or longer, the whole surface changed to present a pale cream color, and those parts forming a large number of conidia presented a pale orange color.

Colonies on malt agar medium, whose composition is given below, achieved a diameter of 30 mm after growth for 7 days at 25° C. The surface of the colony was flat and powdery, in part because of sparse formation of aerial hyphae. The whole surface presented a nearly white coloration.

Colonies on potato dextrose agar medium, whose composition is given below, achieved a diameter of 29 mm after growth for 7 days at 25° C. The surface of the colony was slightly protuberant, because of the prolific and dense formation of hyphae, and the surface was downy. The central part of the colony appeared powdery because of the formation of conidiophores. Almost the whole of the surface was white in color, and the reverse surface was pale yellow. However, the color was deep and dark yellowish at the central parts.

Colonies on lignin cellulose agar medium, whose composition is given below, achieved a diameter of 28 mm after growth for 7 days at 25° C. The surface of the colony was flat. The whole of the surface, other than the central part, was powdery because of the formation of aerial hyphae. The central part became downy on further cultivation. The whole surface was white in color, and the reverse surface was slightly yellowish.

Conidial formation was particularly good on lignin cellulose agar medium after culturing for 10 days at 25° C. The microscopic morphology on lignin cellulose agar medium after culturing for 14 days at 25° C. was as follows.

Conidial formation was dense at the central part of the colony, but turned sparse towards the periphery. The mode of formation was phialidic. Two kinds of conidiophore were formed, one resembling that of *Verticillium* spp., and the other resembling that of *Penicillium* spp. Both kinds of conidiophore were thin, and the surfaces were both smooth and hyaline. In the conidiophores of the Verticillium type, the phialides branched in 3 or 4 directions. The phialides were needle-like, and varied in size from 18.5 to 45 by 1.5 to 3.5 μm. The conidia were elliptical to oval in shape, monocellular and hyaline, and varied in size from 4 to 8.5 by 1.5 to 3.5 μm. The formation of the conidia was concentrated on the phialides, to form drops. In the conidiophores of the Penicillium type, the conidiophores branched in several directions at the top, were flask-like in shape, and had phialides at the end. The phialides were flask-like in shape, were slightly swollen near the basal part, and were from 8.5 to 12.5 by 2.5 μm in size. The conidia were monocellular, hyaline, straight or slightly curved cylindrical in shape, and were from 6 or 6.5 to 8.0 or 10 by 1.5 to 2.5 μm in size. The conidia were formed slantwise and kinked in piles at the top of the phialides, and cylindrical chains were formed on the conidiophores.

These characteristics were compared with those of known strains, and it was found that the characteristics of this new strain accorded well with those of *Clonostachys cylindrospora* Arnaud, as reported by K. Tsubaki in Transactions of the Microbiological Society of Japan, 4 (4),84 (1963). Accordingly, the present strain is considered to be identical to the known strain, *Clonostachys cylindrospora* Arnaud.

A further strain of the genus Clonostachys, *Clonostachys* sp. SANK 18192, is also a preferred microorganism for the production of the desired trans-4-hydroxy-L-proline. This microorganism was isolated from rotten fruit of the species *Aesculus*, which was collected in Sugadaira, Nagano Prefecture, Japan, in September 1991.

*Clonostachys* sp. SANK 18192 has been deposited under the terms of the Budapest Treaty at the Fermentation Research Institute, Agency of Industrial Science and Technology, Japan, on 3rd Dec., 1992, under the accession Number FERMBP-4096.

This strain has the following microbiological properties.

Colonies on modified Weitzman and Silva-Hunter agar medium, whose composition is given below, reached a diameter of 2.5 cm after 7 days growth at 25° C. The colony developed a slight aerial mycelium and mycelial tufts developed towards the margin of the colony, which was thin and complete, resulting in a powdery surface. Both the top surface and the reverse of the colony were a white color, and the colony was thin.

On potato dextrose agar medium, having the composition shown below, the colonies achieved a diameter of 3.2 cm after growth for 7 days at 25° C. The surface of the colony was flocculent and the entire colony was quite thin, with low formation of mycelial tufts. The margin of the colony was also thin, but complete. The top surface of the colony presented a white color, although the reverse surface was a light yellow color.

Teleomorphs of this strain were not observed on any medium.

The formation of conidia on the colony was by a phialidic mode, with two types of conidiophore being formed. The first type resembled the condiophores of *Verticillium* spp. and the second type resembled the conidiophores of *Penicillium* spp. The walls of both types of conidiophore were thin and the surface of the two types was smooth and hyaline. In the conidiophores of the Verticillium type, the phialides branched in three or four directions. The phialides were needle-like, and varied in size from 16.5 to 30 by 2.5 to 3.5 μm. The formation of the conidia was concentrated on the phialides, to form drops. In the conidiophores of the Pencillium type, the conidiophores branched in several directions at the top, were broom-like in shape and had phialides at the end. The phialides were flask-like in shape and were from 7.5 to 12.5 by 1.5 to 3.5 μm in size. The conidia were formed slantwise in a group at the tip of the phialides, and were linked in piles to form chains on the conidiophores. The conidia were cylindrical, monocellular, hyaline and from 5 to 6.5 by 1.5 to 2.5 μm in size.

These characteristics were compared with those of known strains, and it was found that the characteristics of this new strain closely resembled those of *Clonostachys cylindrospora* Arnaud, as reported by K. Tsubaki in Transactions of the Microbiological Society of Japan, 4 (4), 83–90 (1963), and showed all of the characteristics of the genus Clonostachys. Accordingly, this strain was identified as a *Clonostachys* sp.

The strains *Gliocladium* sp. SANK 18092 and *Nectria gliocladioides* Smalley et Hansen SANK 17992 are also useful producers of the desired trans-4-hydroxy-L-proline.

*Gliocladium* sp. SANK 18092 was isolated from a soil sample collected in Isumi-gun, Chiba Prefecture, Japan, in February 1992. The strain was deposited under the terms of the Budapest Treaty at the Fermentation Research Institute, Agency of Industrial Science and Technology, Japan, on 3rd Dec. 1992, and received the accession Number FERM BP-4097.

*Nectria gliocladioides* Smalley et Hansen SANK 17992 was isolated from a sample of rotten wood collected in Awa-gun, Chiba Prefecture, Japan, in February 1992. This strain was deposited under the terms of the Budapest Treaty at the Fermentation Research Institute, Agency of Industrial Science and Technology, Japan, on 3rd Dec. 1992, and received the accession Number FERM BP-4098.

*Gliocladium* sp. SANK 18092 has the following microbiological properties.

Colonies on modified Weitzman and Silva-Hunter agar medium, whose composition is given below, reached a diameter of 4.2 cm after 7 days growth at 25° C. The surface of the colony was flocculent and dense with aerial hyphae. Many mycelial tufts developed towards the margin of the colony, which was quite thick and randomly sinuate. The top surface of the colony was a white color, and the reverse surface was pale yellow in color.

On potato dextrose agar medium, having the composition shown below, the colonies achieved a diameter of 4.4 cm after growth for 7 days at 25° C. The surface of the colony was flocculent and dense with the rich development of aerial hyphae. The margin of the colony was quite thick and randomly sinuate. The colony presented a white color on its top surface, although the reverse surface was a light yellow color.

Teleomorphs of this strain were not observed on any medium.

The formation of conidia on the colony was by a phialidic mode, with two types of conidiophore being formed. The first type resembled the condiophores of *Verticillium* spp. and the second type resembled the conidiophores of *Penicillium* spp. The walls of both types of conidiophore were thin and the surface of the two types was smooth and hyaline. In the conidiophores of the Verticillium type, the phialides branched in three or four directions. The phialides were needle-like, and varied in size from 23 to 31.5 by 1.5 to 3.5 am. The formation of the conidia was concentrated on the phialides, to form drops. In the conidiophores of the Pencillium type, the conidiophores branched in several directions at the top, were broom-like in shape and had phialides at the end. The phialides were flask-like in shape and were from 11.5 to 15 by 2.5 to 3.5 $\mu$m in size. The conidia were formed in a group at the tip of the phialides in the form of a columnar cluster. The conidia were elliptical, monocellular, hyaline and from 5 to 6.5 by 1.5 to 3.5 $\mu$m in size.

These characteristics were compared with those of known strains, and it was found that the characteristics of this new strain closely resembled those of a Gliocladium-type anamorph of *Nectria gliocladioides* Smalley et Hansen, as reported by S. Udagawa and Y. Horie in the Journal of General and Applied Microbiology, 17 141–159 (1971), and this strain showed the characteristics of the genus Gliocladium. The strain was therefore identified as a *Gliocladium* sp.

*Nectria gliocladioides* Smalley et Hansen SANK 17992 has the microbiological properties shown in detail as follows.

Colonies on modified Weitzman and Silva-Hunter agar medium, whose composition is given below, reached a diameter of 4.3 cm after 7 days growth at 25° C. The surface of the colony was flocculent and dense with aerial hyphae. Mycelial tufts developed towards the margin of the colony, which was quite thick and randomly sinuate. Both the top surface and the reverse surface of the colony were a white color.

On potato dextrose agar medium, having the composition shown below, the colonies achieved a diameter of 4.2 cm after growth for 7 days at 25° C. The surface of the colony was flocculent and dense with the rich development of aerial hyphae. The margin of the colony was quite thick and randomly sinuate. The colony presented a white color on its top surface, although the reverse surface was a light yellow color.

On carnation leaf agar, the composition of which is given below, this strain formed a Nectria-type teleomorph. The perithecium was a light yellowish orange color, was formed in clusters on a carnation leaf and was from 200 to 300 $\mu$m in diameter. The peridium was warty, translucent and membranaceous. The ascus was clayate, contained eight ascospores and was from 50 to 60 by 6 to 8 $\mu$m in size. The ascospores were two-celled, hyaline and from 10 to 12 by 3.5 to 4 $\mu$m in size.

An anamorph was formed.

The formation of conidia on the colony was by a phialidic mode; with two types of conidiophore being formed. The first type resembled the condiophores of *Verticillium* spp. and the second type resembled the conidiophores of *Penicillium* spp. The walls of both types of conidiophore were thin and the surface of the two types was smooth and hyaline. In the conidiophores of the Verticillium type, the phialides branched in three or four directions. The phialides were needle-like, and varied in size from 20 to 30 by 2.5 to 3.5 $\mu$m. The formation of the conidia was concentrated on the phialides, to form drops. In the conidiophores of the Pencillium type, the conidiophores branched in several directions at the top, were broom-like in shape and had phialides at the end. The phialides were flask-like in shape and were from 10 to 13.5 by 1.5 to 2 $\mu$m in size. The conidia were formed in a group at the tip of the phialides in the form of a columnar cluster. The conidia were elliptical, monocellular, hyaline and from 5 to 6.5 by 1.5 to 3.5 $\mu$m in size.

These characteristics were compared with those of known strains, and it was found that the characteristics of this new strain accorded well with those of *Nectria gliocladioides* Smalley et. Hansen, as reported by S. Udagawa and Y. Horie in the Journal of General and Applied Microbiology, 17 141–159 (1971). This strain is therefore considered to be identical with the known strain *Nectria gliocladioides* Smalley et Hansen.

The compositions of the media employed above are as shown below.

| Potato dextrose agar medium | |
|---|---|
| potato dextrose agar (product of Nissui) | 39 g |
| distilled water to | 1000 ml |
| Lignin cellulose agar medium: | |
| Glucose | 1 g |
| KH$_2$PO$_4$ | 1 g |
| MgSO$_4$.7H$_2$O | 0.2 g |
| KCl | 0.2 g |
| NaNO$_3$ | 2 g |
| Yeast extract | 0.2 g |
| Agar | 20 g |
| distilled water to | 1000 ml |
| pH: 6.5–7.0 (adjusted with KOH) | |
| Modified Weitzman and Silva-Hunter agar medium: | |
| Oatmeal | 10 g |
| KH$_2$PO$_4$ | 1 g |
| MgSO$_4$.7H$_2$O | 1 g |
| NaNO$_3$ | 1 g |
| Agar | 20 g |
| distilled water to | 1000 ml |
| Malt agar medium: | |
| Malt extract | 2 g |
| Agar | 20 g |
| distilled water to | 1000 ml |

Carnation Leaf Agar

The leaves of a carnation were cut into pieces of about 5 by 5 mm, dried at about 50° C. for several hours and then sterilized by treatment with ethylene oxide gas for 2 hours. The resulting leaf pieces were inocluated onto 2% plain agar.

It will be appreciated that these strains, or any other strain capable of producing trans-4-hydroxy-L-proline, may be sub-cultured or biotechnologically altered or modified to produce an organism with different characteristics. The only requirement is that the resulting organism be capable of producing the required compound. Alterations may occur naturally or artificially, by induction.

Such alterations and modifications may take any desired form, or may be consequent on such considerations as culture conditions, for example. Strains may be modified by culture and so selected as to exhibit such characteristics as enhanced growth, or growth at lower/higher temperatures.

Biotechnological modifications will generally be intentional, and may introduce selectable characteristics, such as bacteriostat resistance or susceptibility, or combinations thereof, in order to maintain purity, or to allow purification of cultures, especially seed cultures, from time to time.

Other characteristics which may be introduced by genetic manipulation are any that are permissible in *Clonostachys, Gliocladium* and *Nectria* spp. For example, plasmids encoding resistances may be incorporated, or any naturally occurring plasmids may be removed. Advantageous plasmids include those that confer auxotrophy. Plasmids may be obtained from any suitable source, or may be engineered by isolating a naturally occurring Clonostachys, Gliocladium or Nectria plasmid and inserting a desired gene or genes from another source. Natural plasmids may also be modified in any other manner that may be considered desirable.

It is also well known that molds mutate easily in natural circumstances or by artificial manipulation (for example, by ultraviolet irradiation, ionizing radiation or chemical treatment). This also applies to the microorganisms employed in the present invention. Accordingly, the present invention also embraces the use of such mutant strains, provided only that they share with the strains described above the characteristic ability to produce trans-4-hydroxy-L-proline.

Any such modified strain may be employed in the process of the present invention, provided only that the strain is capable of producing trans-4-hydroxy-L-proline, a matter which can readily be ascertained by simple and routine experimentation.

In order to obtain trans-4-hydroxy-L-proline from a culture of a suitable microorganism, the microorganism should be fermented in a suitable medium. Such media are generally well known in the art, and will frequently be of a type commonly used in the production of other fermentation products.

Typically, it will be necessary for the medium to comprise any combination of a carbon source, a nitrogen source and one or more inorganic salts assimilable by the relevant microorganism. The minimum requirement for the medium will be that it contains those ingredients essential for the growth of the microorganism, a matter which can readily be ascertained by routine experimentation.

Suitable carbon sources include, for example: glucose, fructose, maltose, sucrose, mannitol, glycerol, dextrin, oatmeal, rye, corn starch, potato, potato starch, corn flour, soybean meal, cottonseed oil, molasses, citric acid and tartaric acid, any of which may be employed alone or in combination with any one or more others. Typical amounts will be in a range from about 1 to 10% w/v of the amount of medium, although the amount may be varied as desired and in accordance with the desired result.

Suitable nitrogen sources include any substance containing a protein, for example, or other readily assimilable source of nitrogen. Representative examples of nitrogen sources are organic nitrogen sources from animals and plants, and may be extracts from such natural sources as soybean meal, wheat bran, peanut meal, cottonseed meal, cottonseed oil, casein hydrolysate, fermamine, fish meal, corn steep liquor, peptone, meat extract, yeast, yeast extract and malt extract; and such inorganic nitrogen sources as sodium nitrate, ammonium nitrate and ammonium sulfate. As with the carbon source, these may be employed alone or in any combination. Suitable amounts are typically within a range from about 0.2 to 6% w/v of the amount of medium, although the amount may be varied as desired and in accordance with the desired result.

Suitable nutrient inorganic salts are those which provide trace elements as well as the major constituent of the salt. Preferably, salts should provide such ions as sodium, ammonium, calcium, phosphate, sulfate, chloride and carbonate. Such trace metals as potassium, calcium, cobalt, manganese, iron, magnesium and strontium, or salts capable of providing such ions as bromide, fluoride, borate or silicate ions, may also be present.

If the microorganism is fermented as a liquid culture, it is preferred that an antifoaming agent, such as a silicone oil or vegetable oil, or other suitable surfactant, is employed.

It is preferred that the pH of the culture medium for the cultivation of the above strains of Clonostachys, Gliocladium or Nectria, when used for the production of trans-4-hydroxy-L-proline, should be maintained in the region of pH 5.0 to pH 7.0, although the only substantial requirement is that the pH should not prevent growth of the microorganism, or adversely irreversibly affect the quality of the final product.

Clonostachys, Gliocladium and Nectria, in general, grow at temperatures ranging from 5° C. to 30° C., and grow well at temperatures in the range from 15° C. to 28° C. Other temperatures not falling within these ranges may be applicable where a strain has been developed which can grow at lower or higher temperatures, or for other special purposes, as is well known in the art. For the production of trans-4-hydroxy-L-proline, a preferable temperature is between 23° C. and 28° C.

Trans-4-Hydroxy-L-proline is ideally obtained by aerobic culture, and any suitable aerobic culture techniques, such as, for example, solid culture, shaking culture or aeration-agitation culture, may be employed.

If the culture is conducted on a small scale, then a shaking culture fermented for several days at from 23° C. to 28° C., more preferably about 26° C., is generally preferred.

To start a fermentative culture, a preferred technique employs an initial inoculum prepared in one or two steps, for example, in an Erlenmeyer flask, which is preferably provided with baffles (a water flow controlling wall). A carbon source and a nitrogen source may be used in combination for the culture medium. The seed flask is preferably shaken in a thermostatic incubator at 26° C. for a period of 3 or 4 days, or until sufficient growth is observed. The resulting seed culture may then be used to inoculate a second seed culture, or a production culture. If a second seeding is conducted, this may be performed in a similar manner, and partly used for inoculation to the production medium. The flask into which the seed culture is inoculated is shaken for a suitable period, for example from 3 to 12 days, preferably from 9 to 10 days, or until maximal production is obtained, at a suitable temperature, for example 26° C. When incubation is complete, the contents of the flask may be collected by suitable conventional means, for example centrifugation or filtration.

If the culture is to be performed on a large scale, cultivation in a suitable aeration-agitation fermenter may be preferable. In this procedure, the nutrient medium can be prepared in the fermenter. The medium is first sterilized by heating to an appropriate high temperature, for example at 125° C., after which it is cooled and seeded with an inoculum previously grown on a sterilized medium, as described above. The culture is preferably performed at a temperature from 23° C. to 26° C., preferably about 26° C., with stirring and aeration. This procedure is suitable for obtaining a large amount of the compound.

The amount of the trans-4-hydroxy-L-proline produced by the culture with the passage of time can be monitored by sampling and assessing by conventional means. In general, the amount of trans-4-hydroxy-L-proline produced reaches a maximum after a period of time of between 72 hours and 240 hours.

If any microorganism is to be cultured in order to determine whether the microorganism itself produces trans-4-hydroxy-L-proline or not, it is important that the medium used for this cultivation should not contain peptone or malt extract of animal origin, since this already contains trans-4-hydroxy-L-proline as a component.

After completion of the cultivation, the desired compound can be collected, analyzed quantitatively, separated and purified by any conventional means.

For example, in more detail, after cultivation, the trans-4-hydroxy-L-proline present in the liquid part (and possibly in the cellular part) of the culture liquid is separated as follows: the culture broth is mixed with an organic solvent, such as acetone, and the liquid is separated from the cellular part and from other solid matter, for example by filtration optionally using diatomite as a filter aid or by centrifugation, and then the trans-4-hydroxy-L-proline is extracted and purified from the resulting filtrate or supernatant making use of its physicochemical properties.

For example, trans-4-hydroxy-L-proline can be obtained by passing the filtrate or supernatant through a column of an anion exchange resin, such as DEAE-Toyopearl (Toyopearl is a trade name for a product of Toso), to remove any impurities by adsorption. trans-4-Hydroxy-L-proline may also be obtained by adsorbing the filtrate or supernatant on a cation exchange resin column, such as Dowex 50W×4 (Dowex is a trade name for a product of Dow Chemical Co.), and then eluted the desired trans-4-hydroxy-L-proline with aqueous ammonia. Amberlite IRC-50, CG-50 (Amberlite is a trade name for a product of Rohm & Haas), Dowex SBR-P (Dow Chemical Co.) and other ion exchange resin can also be employed to obtain trans-4-hydroxy-L-proline. Alternatively, active carbon or an adsorbent resin, such as Amberlite XAD-2, XAD-4 (Rohm a Haas) or Diaion HP-10, HP-20, CHP-20, HP-50 (Diaion is a trade name for a product of Mitsubishi Kasei) may be employed to purify the trans-4-hydroxy-L-proline. trans-4-Hydroxy-L-proline can be obtained by passing the liquid containing the desired compound through a column of an adsorbent, such as those mentioned above, to remove any impurities by adsorption; or the trans-4-hydroxy-L-proline may be adsorbed, and then eluted with a mixed solvent comprising water and an organic solvent, such as aqueous methanol or aqueous acetone.

The trans-4-hydroxy-L-proline thus obtained can be further purified by various conventional means, for example adsorption column chromatography using a carrier, such as silica gel or Floridil (trade name), by partition or molecular sieve column chromatography using Apisel (Apisel is a trade name for a product of Asahi Kasei) or Sephadex G-10 (Sephadex is a trade name for a product of Pharmacia Co.), or by high performance liquid chromatography using a normal phase or reverse phase column or an ion exchange column.

The target compound can be analyzed quantitatively by the following procedure.

First, the primary amino acids are converted into their derivatives by treatment with ortho-phthalaldehyde in the presence of mercaptopropionic acid, and then the remaining secondary amino acids (proline and hydroxyproline) are converted into their FMOC (9-fluorenylmethyl chloroformate) derivatives by treatment with FMOC. Only secondary amino acids (proline and hydroxyproline) can be analyzed quantitatively with a high sensitivity by fluorometry at 266 nm for excitation and 305 nm for determination both of which are specific to FMOC. These procedures were carried out using an amino acid analysis system sold as "Amino-Quant" by Hewlett Packard.

The invention is further illustrated by the following non-limiting Examples.

EXAMPLE 1

*Clonostachys cylindrospora* SANK 14591 was inoculated in a 500 ml Erlenmeyer flask, fitted with a baffle and containing 100 ml of GPMY medium, the components of which are shown below, and the microorganism was cultured at 26° C. with shaking at a rotation rate of 200 rpm.

| Components of GPMY medium: | |
| --- | --- |
| Glycerol | 50 g |
| Raw potato | 50 g |
| Malt extract | 5 g |
| Yeast extract | 5 g |
| Tap water | 1000 ml |

Six days after the beginning of the cultivation, the amount of trans-4-hydroxy-L-proline present in the culture liquid containing the microbial cells was determined.

The quantitative determination was performed using the method described generally above. In more detail, 5 $\mu$l of a borate buffer solution made by Hewlett Packard (Cord No.: 5061-3339), 1 $\mu$l of OPA reagent made by Hewlett Packard (Cord No.: 5061-3335) and 1 $\mu$l of the filtrate obtained by filtration of a 5-fold diluted culture liquid through Sephpak Plus (Waters Millipore) were mixed together and stirred. 1 $\mu$l of FMOC reagent made by Hewlett Packard (Cord No.: 5061-3337) was added to this mixture, and then separated by means of an AminoQuant Column (Hewlett Packard). By fluorometry of the eluted solution at wave lengths of 266 nm for excitation and 305 nm for determination, the secondary amino acids (proline and hydroxyproline) alone can be determined. The retention time of the FMOC derivative of trans-4-hydroxy-L-proline was found to be 11.20 minutes.

The quantitative analysis was carried out using an AminoQuant HP1090M and Fluorometer HP1046A (both made by Hewlett Packard).

The analysis showed the presence of 12.9 $\mu$g/ml of trans-4-hydroxy-L-proline in the culture liquid.

EXAMPLE 2

In a similar way to that described in Example 1, *Clonostachys cylindrospora* SANK 14591 was cultured at 26° C. with shaking at a rotation rate of 200 rpm. The 1.8 liters of culture liquid thus obtained were mixed with 2 liters of acetone and allowed to stand overnight at 4° C. The mixture was then filtered using a Celite (trade mark) filter aid, and the filtrate was condensed by evaporation Under reduced pressure. There were thus obtained 500 ml of a crude extract, which was adsorbed on a Dowex 50W column and eluted with 0.5N aqueous ammonia. The eluate was condensed by evaporation under reduced pressure.

The residue thus obtained was subjected to gel filtration, using Sephadex G-10, at a flow rate of 60 ml/hour and Using a mixed solvent consisting of butanol, acetic acid and water, in proportions of 4:1:2 by volume as the mobile phase. Those fractions containing the desired trans-4-hydroxy-L-proline were collected and condensed by evaporation under reduced pressure. The resulting residue was subjected to gel filtration, using Sephadex G-10, at a flow rate of 15 ml/hour and using a mixed solvent consisting of butanol, acetic acid and water, in proportions of 5.5:1:2 by volume as the mobile phase. Those fractions containing trans-4-hydroxy-L-proline were collected and condensed by evaporation under reduced pressure. The resulting residue was subjected to gel filtration, using Sephadex G-10, at a flow rate of 15 µml/hour and using a mixed solvent consisting of butanol, acetic acid and water, in proportions of 6:1:2 by volume as the mobile phase. Those fractions containing trans-4-hydroxy-L-proline were collected, condensed by evaporation under reduced pressure and passed through a DEAE-Toyopearl 650S column. Unadsorbed fractions were collected and condensed by evaporation under reduced pressure. The residue thus obtained was subjected to gel filtration, using Sephadex-G-10, at a flow rate of 15 ml/hour and using a mixed solvent consisting of butanol, acetic acid and water, in proportions of 6:1:2 by volume as the mobile phase. Finally, fractions containing trans-4-hydroxy-L-proline were collected, condensed by evaporation under reduced pressure and passed through a DEAE-Toyopearl 650S column. Unadsorbed fractions were collected and condensed by evaporation under reduced pressure, to afford 1.0 mg of the title compound in pure form.

Nuclear Magnetic Resonance Spectrum (deuterium oxide, using tetradeuterated sodium trimethylsilylpropionate as an internal standard), δ:

2.17 (1H, doubled doublet of doublets, J=14.2, 10.2 & 4.4 Hz);
2.43 (1H, doubled doublet of multiplets, J=14.2 & 7.8 Hz);
3.37 (1H, doublet of multiplets, J=12.7 Hz);
3.49 (1H, doublet of doublets, J=12.7 & 3.9 Hz);
4.35 (1H, doublet of doublets, J=10.1 & 7.8 Hz);
4.67 (1H, multiplet).

The nuclear magnetic resonance spectrum accorded with the known spectrum of trans-4-hydroxy-L-proline.

EXAMPLE 3

Spores of *Nectria gliocladioides* SANK 17992 were inoculated into a 500 ml Erlenmeyer flask, fitted with a baffle and containing 100 ml of GPMY-1 medium, the composition of which is shown below, and the microorganism was cultured at 23° C. with shaking at a rotation rate of 200 rpm.

| Composition of GPMY-1 medium | |
| --- | --- |
| Glycerol | 75 g |
| Raw potato | 75 g |
| Malt extract | 7.5 g |
| Yeast extract | 7.5 g |
| Tap water | 1000 ml |

Nine days after the beginning of the cultivation, the amount of trans-4-hydroxy-L-proline present in the culture liquid Containing the microbial cells was determined.

The quantitative analysis of the trans-4-hydroxy-L-proline was performed using the method described in Example 1. In this case, the retention time of the FMOC derivative of trans-4-hydroxy-L-proline was found to be 11.20 minutes.

The analysis showed the presence of 9.35 µg/ml of trans-4-hydroxy-L-proline in the culture medium of *Nectria gliocladioides* SANK 17992.

EXAMPLE 4

Following a procedure similar to that described in Example 3, *Gliocladium* sp. SANK 18092 was inoculated into a 500 ml Erlenmeyer flask, fitted with a baffle and containing 100 ml of GPMY-1 medium, the composition of which is shown in Example 3, and the microorganism was cultured at 23° C. with shaking at a rotation rate of 200 rpm.

Nine days after the beginning of the cultivation, the amount of trans-4-hydroxy-L-proline present in the culture liquid containing the microbial cells was determined.

The quantitative analysis of the trans-4-hydroxy-L-proline was performed using the method described in Example 1. In this case, the retention time of the FMOC derivative of trans-4-hydroxy-L-proline was found to be 11.20 minutes.

The analysis showed the presence of 8.12 µg/ml of trans-4-hydroxy-L-proline in the culture medium of *Gliocladium* sp. SANK 18092.

We claim:
1. An isolated culture of *Clonostachys* sp. SANK 18192.
2. An isolated culture of *Gliocladium* sp. SANK 18092.

* * * * *